United States Patent
Yan et al.

(10) Patent No.: US 8,309,741 B2
(45) Date of Patent: Nov. 13, 2012

(54) BENZOCARBAZOLE-INTERCALATED LAYERED DOUBLE HYDROXIDES COMPOSITE LUMINESCENT MATERIAL AND ITS PREPARATION METHOD

(75) Inventors: Dongpeng Yan, Beijing (CN); Jun Lu, Beijing (CN); Min Wei, Beijing (CN); Xue Duan, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 533 days.

(21) Appl. No.: 12/459,793

(22) Filed: Jul. 7, 2009

(65) Prior Publication Data

US 2010/0130750 A1  May 27, 2010

(30) Foreign Application Priority Data

Nov. 25, 2008 (CN) .......................... 2008 1 0227218

(51) Int. Cl.
*C07F 5/06* (2006.01)
*C07D 209/82* (2006.01)
(52) U.S. Cl. ....................................... 548/402; 548/440
(58) Field of Classification Search .................. 548/402, 548/440
See application file for complete search history.

(56) References Cited

PUBLICATIONS

Yan et al. "Sulforhodamine B Intercalated Layered Double Hydroxide Thin Film with Polarized Photoluminescence" Journal of Physical Chemistry B, 2009, vol. 113, pp. 1381-1388.*
Yan et al. "Benzocarbazole anions intercalated layered double hydroxide and its tunable fluorescence" Physical Chemistry Chemical Physics, 2010, vol. 12, pp. 15085-15092.*

* cited by examiner

*Primary Examiner* — Joseph Kosack
(74) *Attorney, Agent, or Firm* — Blakely, Sokoloff, Taylor & Zafman LLP

(57) ABSTRACT

The present invention discloses a benzocarbazole-intercalated layered double hydroxides (LDHs) composite luminescent material and its preparation method. The detailed procedure comprises preparing divalent and trivalent metal cation solution A and glycol solution B of sodium 2-hydroxy benzo[a]carbazole-3-carboxylate, mixing the solutions A and B to obtain solution C, slowly adding the prepared NaOH solution dropwise into the solution C, regulating pH of the resultant after dropwise addition to obtain slurry D, allowing the slurry D to react under water bath or microwave temperature-controlled heating condition, centrifuging and washing the obtained product, and drying in vacuum to obtain 2-hydroxy benzo[a]carbazole-3-carboxylate anion intercalated LDHs composite material. The method implements the immobilization of sodium 2-hydroxy benzo[a]carbazole-3-carboxylate, effectively improves thermal stability of the luminescent dye molecules, and reduces fluorescence quenching caused by aggregation of the dye molecules.

2 Claims, 3 Drawing Sheets

BENZOCARBAZOLE-INTERCALATED LAYERED DOUBLE HYDROXIDES COMPOSITE LUMINESCENT MATERIAL AND ITS PREPARATION METHOD

CROSS-REFERENCE TO RELATED APPLICATION

The present patent application claims priority from Chinese Patent Application No. 200810227218.5, filed on Nov. 25, 2008.

FIELD OF THE INVENTION

The present invention relates to the field of inorganic-organic composite luminescent material, and particularly provides a benzocarbazole-intercalated layered double hydroxides composite luminescent material and its preparation method.

BACKGROUND OF THE INVENTION

Owing to advantages of high luminance, simple structure, low driving voltage, and wide view angle, organic electroluminescent device has drawn more and more attention for its application in flat panel display. Research and development of various organic luminescent compounds and luminescent metal coordination compound provides premise for obtaining luminescent device with high luminance, high efficiency, full color, and high stability. Fluorescent dyes with good electroluminescent efficiency are widely applied in preparation of organic electroluminescent device, which greatly promotes the development of organic electroluminescent device.

Carbazole dyes is a kind of blue electroluminescent material with high performance, which has very high fluorescence quantum efficiency, narrow luminescent wavelength range, high color purity, and fluorescence emission wavelength at about 450 nm (pure blue light). Carbazole and its derivatives belong to large conjugated system and have strong intramolecular electron transfer ability, which have been studied, developed, and applied as a good optical material, such as they can be applied as π donor to form charge transfer type complex with n acceptor of special performance, and they are novel photoelectric materials receiving wide attention. At the same time, carbazoles have good hole transport performance, and their derivatives have high glass transition temperature, and have already been adopted for manufacturing blue electroluminescent device with high performance.

However, dye-type luminescent material is prone to the formation of aggregate in general solution state, which is unfavorable for high efficiency luminance of dye molecules. If dye molecules are uniformly distributed as guest in a host material, their luminous efficiency can be largely improved. Therefore, formation of organic-inorganic composite via introduction of negatively charged dye molecules into layers of layered double hydroxides can realize oriented arrangement and uniform dispersion of dye molecules in molecular scale, and can also improve physical and chemical stability of dye molecules. However, the research regarding introduction of carbazoles or its derivatives dye molecules into layers of layered double hydroxides has not been reported until now.

SUMMARY OF THE INVENTION

The object of the present invention is to provide benzocarbazole-intercalated layered double hydroxides (LDHs) composite luminescent material and its preparation method. The material is characterized by its chemical formula: $[(M^{2+})_{1-x}(M^{3+})_x(OH^-)_2]^{x+}(A^-)_x \cdot mH_2O$, wherein $0.1 \leq x \leq 0.33$, m is number of interlayer crystallization water molecules, and m=0.5-6 (such as 0.5-3 or 3-6), $M^{2+}$ is divalent metal cation, $M^{3+}$ is trivalent metal cation, and $A^-$ is 2-hydroxy benzo[a]carbazole-3-carboxylate anion. And the composite luminescent material has crystal structure of LDHs-type material, in which metal cations and hydroxide anions form multiple octahedrons via covalent bonds, the multiple octahedrons form sheet-like structure via sharing edge, and 2-hydroxy, benzo[a]carbazole-3-carboxylate anions are intercalated into LDHs layers to form anionic type intercalated supramolecular layered luminescent material with 2-hydroxy benzo[a] carbazole-3-carboxylate anion uniformly dispersion.

The preparation method in the present invention comprises following steps:

(1) Preparing solution A with divalent metal cation $M^{2+}$/trivalent metal cation $M^{3+}$ molar ratio of 2:1-4:1, wherein $M^{2+}$ concentration is 0.01-1.6 mol/L;

(2) Preparing anhydrous ethylene glycol solution B of sodium 2-hydroxy benzo[a]carbazole-3-carboxylate, with concentration of 0.01-2.0M;

(3) Mixing solutions A and B to give solution C, pouring solution C into four-neck flask, wherein the usage amount of solutions A and B makes the molar ratio of sodium 2-hydroxy benzo[a]carbazole-3-carboxylate/trivalent metal cation $M^{3+}$ in the solution C within 1:1-3:1;

(4) Preparing 0.01-3.0 mol/L NaOH solution, slowly adding the NaOH solution dropwise into the four-neck flask under nitrogen gas protection via constant-pressure funnel, wherein the usage amount of the solution C and NaOH solution makes the molar ratio of NaOH/sum of $M^{3+}$ and $M^{2+}$ at 2;

(5) Regulating pH of the mixed solution obtained in (4) by NaOH to 8.0-10.0 after finishing the dropwise addition to obtain slurry D, placing the four-neck flask with the slurry D into 50~80° C. water bath, reacting under nitrogen gas protection for 12-24 hr, or transferring the slurry D from the four-neck flask into microwave rapid digestion tank, and microwave heating to react for 2-5 hr at 80~100° C.; and (6) Subjecting the reaction product obtained in (5) to solid-liquid separation, sequentially washing the obtained solid product with $CO_2$-free deionized water and ethylene glycol for 3-6 times until the washing liquid is colorless, centrifuging after each washing, drying in vacuum the filter cake resulted from centrifugation after the final washing at 50~70° C. for 15-20 hr to give 2-hydroxy benzo[a]carbazole-3-carboxylate anion intercalated LDHs composite luminescent material.

In step (6), the solid-liquid separation method can be routine various solid-liquid separation methods, preferably centrifugation.

The $M^{2+}$ in the present invention is preferably $Mg^{2+}$, $Ni^{2+}$, $Co^{2+}$, $Zn^{2+}$, or $Ca^{2+}$, and $M^{3+}$ is preferably $Al^{3+}$ or $Fe^{3+}$.

The present invention has the advantages that luminescent dye 2-hydroxy benzo[a]carbazole-3-carboxylate anions are introduced into layers of LDHs, restricted space among LDHs layers and host-guest interaction are utilized to achieve the immobilization of 2-hydroxy benzo[a]carbazole-3-carboxylate anions while reducing fluorescence quenching caused by dye molecule aggregate, which provides theoretical research basis for the application of LDHs in the field of solid dye luminescent device.

DETAILED DESCRIPTION OF THE EMBODIMENTS

Figure 1:
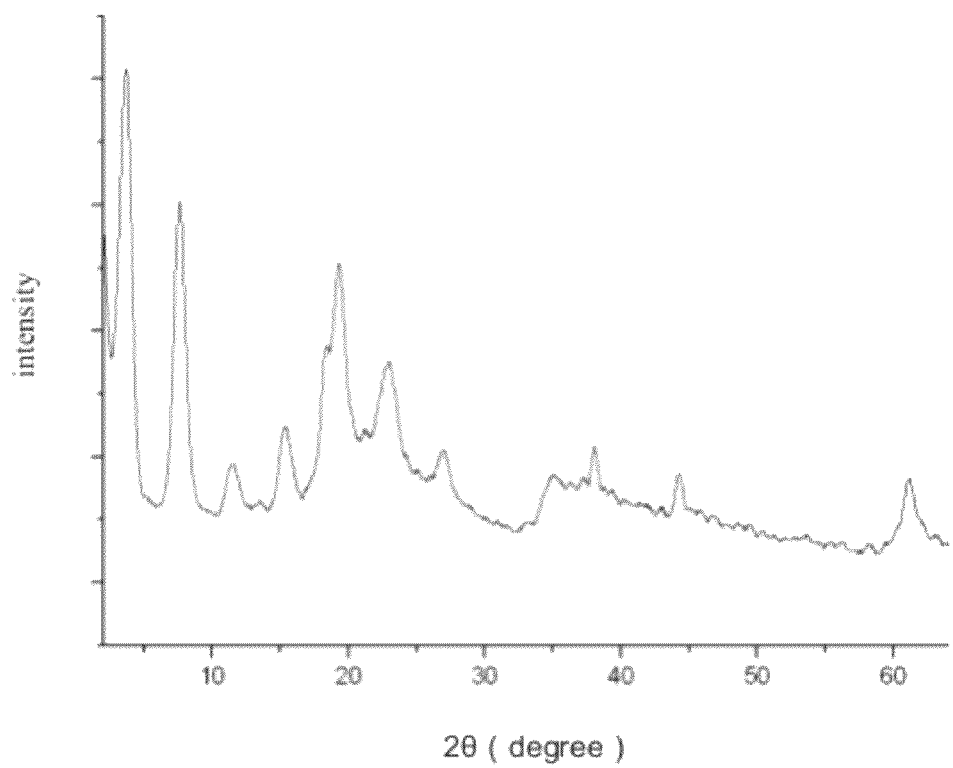
FIG. 1 is the XRD pattern of 2-hydroxy benzo[a]carbazole-3-carboxylate anion intercalated LDHs composite luminescent material obtained in example 1 of the present invention.

The present invention adopts coprecipitation method to intercalate 2-hydroxy benzo[a]carbazole-3-carboxylate anions into LDHs layers to form uniformly dispersed 2-hydroxy benzo[a]carbazole-3-carboxylate anion intercalated anionic type supramolecular layered composite luminescent material. The composite luminescent material is characterized and analyzed as below: 1. XRD characterization, in which the interlayer spacing is calculated as 2.3-2.5 nm, which demonstrates that 2-hydroxy benzo[a]carbazole-3-carboxylate anions are successfully intercalated into LDHs layers; 2. fluorescence spectroscopy characterization, which shows that the luminescent peak of the composite luminescent material has remarkable red-shift characteristics compared to its aqueous solution; 3. TG-DTA analysis, which shows that the thermal decomposition temperature of the composite luminescent material is significantly enhanced compared with that of pure sodium 2-hydroxy benzo[a]carbazole-3-carboxylate. The above characterization and analysis results show that the composite luminescent material fully utilizes restricted space among LDHs layers and host-guest interaction to achieve the immobilization of dye molecule while improving the mechanical strength and physical and chemical stability of the dye.

The present invention will be further explained through following examples.

Example 1

1. Weighing $Mg(NO_3)_2 \cdot 6H_2O$ 1.282 g and $Al(NO_3)_3 \cdot 9H_2O$ 0.938 g, dissolving them in $CO_2$-free deionized water of 100 ml to obtain solution A with $Mg^{2+}/Al^{3+}$ molar ratio of 2:1 and $Mg^{2+}$ concentration of 0.05M;
2. Dissolving sodium 2-hydroxy benzo[a]carbazole-3-carboxylate 0.898 g in 100 ml anhydrous ethylene glycol to obtain solution B with concentration of 0.03M, wherein sodium 2-hydroxy benzo[a]carbazole-3-carboxylate/$Al^{3+}$ molar ratio is 1.2:1;
3. Mixing the solutions A and B to obtain solution C, and pouring the solution C into four-neck flask;
4. Dissolving NaOH 0.6 g in $CO_2$-free deionized water 100 ml, and slowly adding the NaOH solution dropwise into the four-neck flask containing the solution C under nitrogen gas protection via constant-pressure funnel;
5. Regulating pH of the mixed solution obtained in step 4 by NaOH to 8.0 after dropwise addition to obtain slurry D, placing the four-neck flask in 70° C. water bath, and reacting for 24 hr under nitrogen gas protection; and
6. Centrifuging the reaction product in step 5, washing the obtained filter cake respectively with $CO_2$-free deionized water and ethylene glycol for 6 times until the washing liquid is colorless, centrifuging after each washing, drying in vacuum the filter cake obtained by centrifugation after the final washing at 70° C. for 20 hr to give 2-hydroxy benzo[a]carbazole-3-carboxylate anion intercalated LDHs composite luminescent material with chemical formula of $[(Mg^{2+})_{0.67}(Al^{3+})_{0.33}(OH^-)_2]^{0.33+}(A^-)_{0.33} \cdot 0.7H_2O$ ($A^-$ represents benzocarbazole anion).

The product is characterized as follows.

XRD-6000 XRD spectrometer (SHIMADZU, Japan) is adopted to give XRD of 2-hydroxy benzo[a]carbazole-3-carboxylate anion intercalated LDHs composite luminescent material, as shown in FIG. 1. It can be observed from FIG. 1 that the XRD pattern of 2-hydroxy benzo[a]carbazole-3-carboxylate anion intercalated LDHs composite luminescent material shows series 00l oriented diffraction peaks, 003 diffraction peak occurs at 3.6°, the calculated interlayer spacing is 2.34 nm, and interference of carbonate entering into LDHs layers is eliminated, which proves that 2-hydroxy benzo[a]carbazole-3-carboxylate anions are successfully intercalated into LDHs layers.

Figure 3:
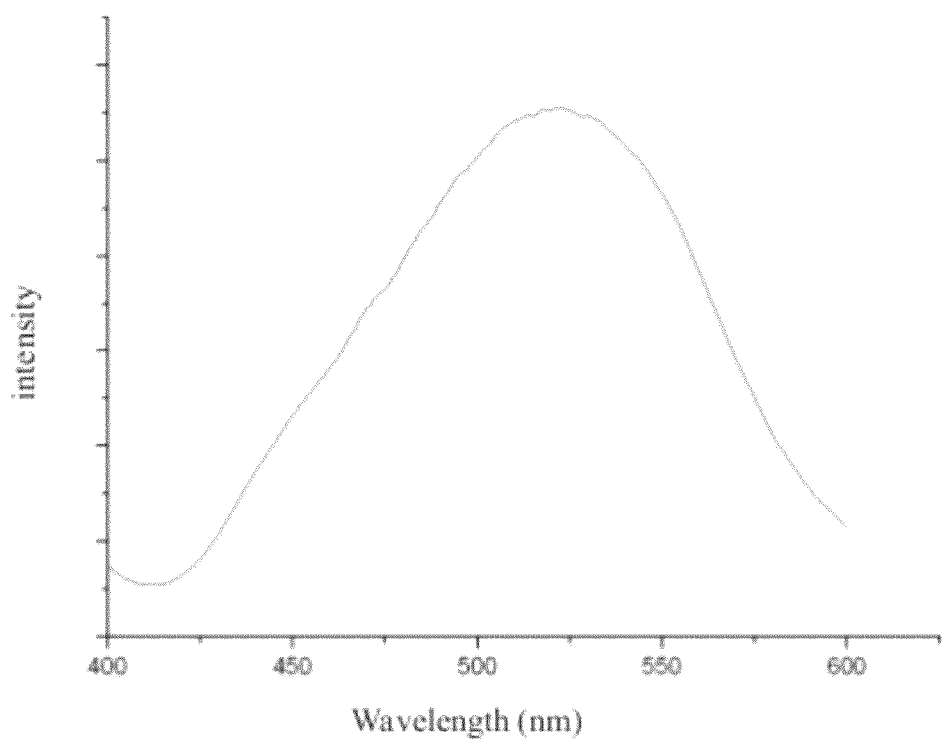
FIG. 3 is the fluorescence emission spectrum of 2-hydroxy benzo[a]carbazole-3-carboxylate anion intercalated LDHs composite luminescent material with 395 nm UV excitation obtained in example 1 of the present invention.

RF-5301PC fluorescence spectrophotometer (SHIMADZU, Japan) is utilized to give fluorescence spectra of 2-hydroxy benzo[a]carbazole-3-carboxylate anion intercalated LDHs composite luminescent material, as shown in FIG. 3. It can be observed from FIG. 3 that the fluorescence emission spectrum of 2-hydroxy benzo[a]carbazole-3-carboxylate anion intercalated LDHs composite luminescent material shows peaks at 525 nm with 395 nm UV excitation, and shows obvious red-shift effect compared with that of dilute solution of pure sodium 2-hydroxy benzo[a]carbazole-3-carboxylate, which further proves that 2-hydroxy benzocarbazole-3-carboxylate anions are successfully intercalated into LDHs layers.

Example 2

1. Weighing $Mg(NO_3)_2 \cdot 6H_2O$ 1.923 g and $Al(NO_3)_3 \cdot 9H_2O$ 0.938 g, dissolving them in $CO_2$-free deionized water 50 ml to obtain solution A with $Mg^{2+}/Al^{3+}$ molar ratio of 3:1 and $Mg^{2+}$ concentration of 0.15M;
2. Dissolving sodium 2-hydroxy benzo[a]carbazole-3-carboxylate 1.347 g in anhydrous ethylene glycol 150 ml to obtain solution B with concentration of 0.03M, wherein sodium 2-hydroxy benzo[a]carbazole-3-carboxylate/$Al^{3+}$ molar ratio is 1.8:1;
3. Mixing the solutions A and B to obtain solution C, and pouring the solution C into four-neck flask;
4. Dissolving NaOH 0.6 g in $CO_2$-free deionized water 50 ml, and slowly adding the NaOH solution dropwise into the four-neck flask containing the solution C under nitrogen gas protection via constant-pressure funnel;
5. Regulating pH of the mixed solution obtained in step 4 by NaOH to 10.0 after dropwise addition to obtain slurry D, placing the four-neck flask in 50° C. water bath, and reacting for 12 hr under nitrogen gas protection; and
6. Centrifuging the reaction product in step 5, washing the obtained filter cake respectively with $CO_2$-free deionized water and ethylene glycol for 6 times until the washing liquid is colorless, centrifuging after each washing, drying in vacuum the filter cake obtained by centrifugation after the final washing at 50° C. for 15 hr to give 2-hydroxy benzo[a]carbazole-3-carboxylate anion intercalated LDHs composite luminescent material with chemical formula of $[(Mg^{2+})_{0.75}(Al^{3+})_{0.25}(OH^-)_2]^{0.25+}(A^-)_{0.25} \cdot 0.95 H_2O$ ($A^-$ represents benzocarbazole anion).

The product is characterized as follows.

Figure 2:
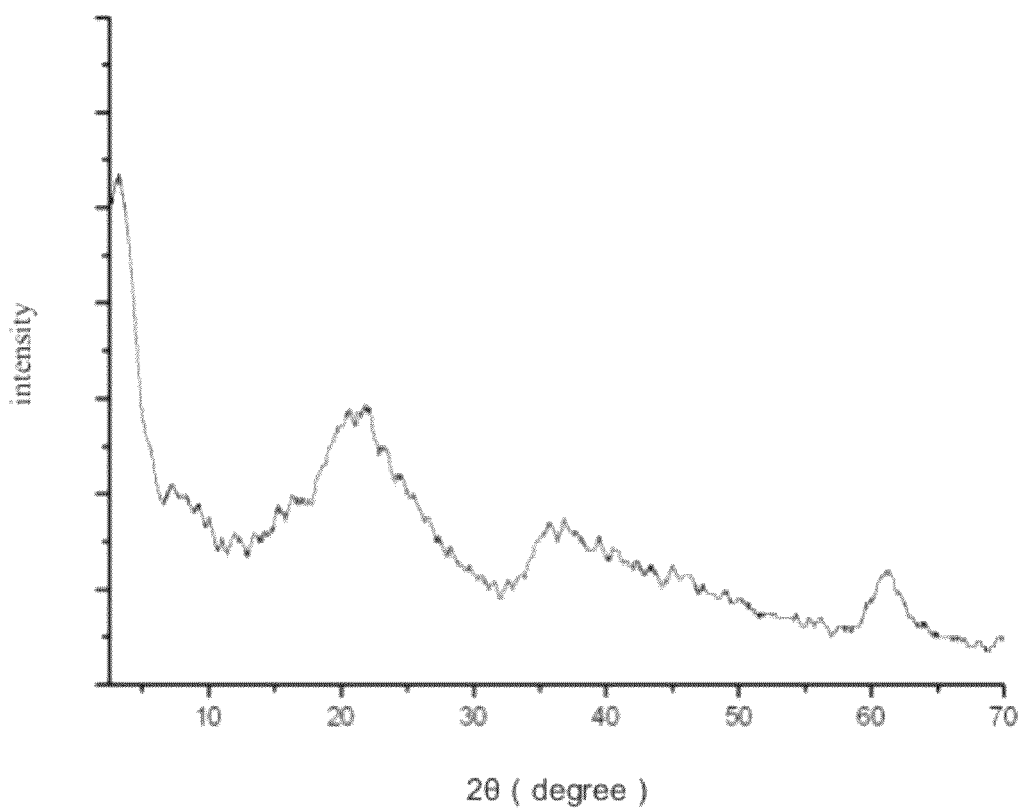
FIG. 2 is the XRD pattern of 2-hydroxy benzo[a]carbazole-3-carboxylate anion intercalated LDHs composite luminescent material obtained in example 2 of the present invention.

XRD-6000 XRD spectrometer (SHIMADZU, Japan) is adopted to give XRD pattern of 2-hydroxy benzo[a]carbazole-3-carboxylate anion intercalated LDHs composite luminescent material, as shown in FIG. 2. It can be observed from FIG. 2 that the XRD pattern of 2-hydroxy benzo[a]carbazole-3-carboxylate anion intercalated LDHs composite luminescent material shows series 001 oriented diffraction peaks, 003 diffraction peak occurs at about 3.6°, and interference of carbonate entering into LDHs layers is eliminated, which proves that 2-hydroxy benzo[a]carbazole-3-carboxylate anions are successfully intercalated into LDHs layers.

Figure 4:
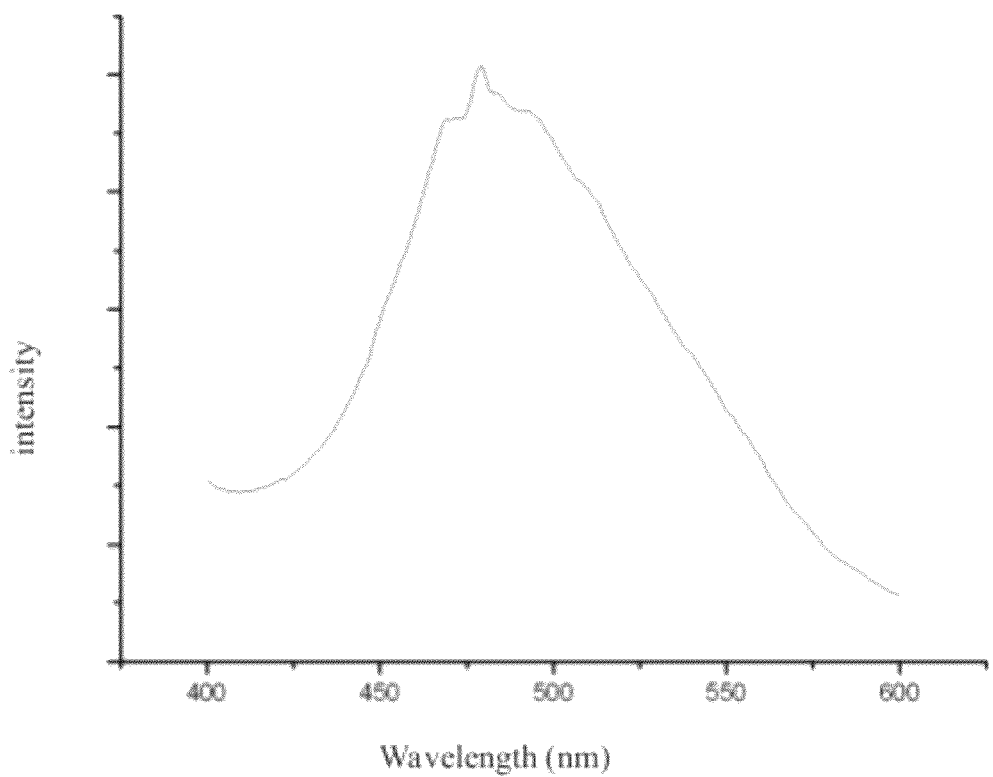
FIG. 4 is the fluorescence emission spectrum of 2-hydroxy benzo[a]carbazole-3-carboxylate anion intercalated LDHs composite luminescent material with 395 nm UV excitation obtained in example 2 of the present invention.

RF-5301PC fluorescence spectrophotometer (SHIMADZU, Japan) is utilized to give fluorescence spectra of 2-hydroxy benzo[a]carbazole-3-carboxylate anion intercalated LDHs composite luminescent material, as shown in FIG. 4. It can be observed from FIG. 4 that the fluorescence emission spectrum of 2-hydroxy benzo[a]carbazole-3-carboxylate anion intercalated LDHs composite luminescent material shows peaks at 480 nm with 395 nm UV excitation, and shows non-obvious red-shift effect compared with that of dilute solution of pure sodium 2-hydroxy benzo[a]carbazole-3-carboxylate.

Example 3

1. Weighing $Mg(NO_3)_2 \cdot 6H_2O$ 1.282 g and $Al(NO_3)_3 \cdot 9H_2O$ 0.938 g, dissolving them in $CO_2$-free deionized water 100 ml to obtain solution A with $Mg^{2+}/Al^{3+}$ molar ratio of 2:1 and $Mg^{2+}$ concentration of 0.05M;
2. Dissolving sodium 2-hydroxy benzo[a]carbazole-3-carboxylate 1.871 g in anhydrous glycol 150 ml to obtain solution B with the concentration of 0.04M, wherein sodium 2-hydroxy benzo[a]carbazole-3-carboxylate/$Al^{3+}$ molar ratio is 2.5:1;
3. Mixing the solutions A and B to obtain solution C, and pouring the solution C into four-neck flask;
4. Dissolving NaOH 0.6 g in $CO_2$-free deionized water 150 ml, and slowly adding the NaOH solution dropwise into the four-neck flask containing the solution C under nitrogen gas protection via constant-pressure funnel;
5. Regulating pH of the mixed solution obtained in step 4 by NaOH to 8.0 after dropwise addition finished to obtain slurry D, transferring slurry D to microwave rapid digestion tank, and microwave heating to react at 90° C. for 3 hr;
6. Centrifuging the reaction product in step 5, washing the obtained filter cake respectively with $CO_2$-free deionized water and ethylene glycol for 5 times until the washing liquid is colorless, centrifuging after each washing, drying in vacuum the filter cake obtained by centrifugation after the final washing at 70° C. for 18 hr to obtain 2-hydroxy benzo[a]carbazole-3-carboxylate anion intercalated LDHs composite luminescent material with chemical formula of $[(Mg^{2+})_{0.67}(Al^{3+})_{0.33}(OH^-)_2]^{0.33+}(A^-)_{0.33} \cdot 0.83 H_2O$ ($A^-$ represents benzocarbazole anion).

The product is subjected to TG-DTA analysis by using PCT-1A computer differential thermal balance, and the test conditions include air atmosphere, temperature elevation range of 30-600° C., and temperature elevation rate of 10° C./min.

Figure 5:
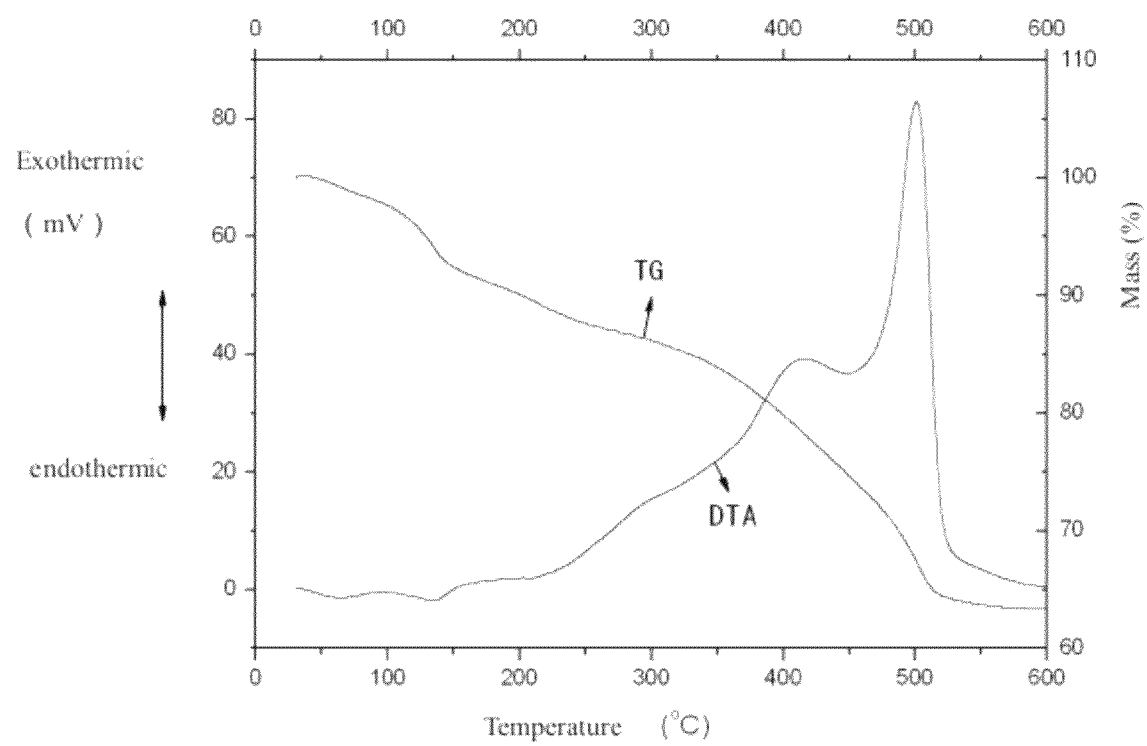
FIG. 5 is the TG-DTA curve of the 2-hydroxy benzo[a] carbazole-3-carboxylate anion intercalated LDHs composite luminescent material obtained in example 3 of the present invention.

As shown in FIG. 5, TG-DTA curve shows that thermal decomposition temperature of 2-hydroxy benzo[a]carbazole-3-carboxylate anion intercalated into LDHs layers is 430° C., which is higher than thermal decomposition temperature (350° C.) of pure sodium 2-hydroxy benzocarbazole-3-carboxylate by 80° C., which shows that the thermal stability of the dye molecule is significantly enhanced.

What is claimed is:

1. A benzocarbazole-intercalated layered double hydroxides (LDHs) composite luminescent material, wherein the chemical formula of the composite luminescent material is $[(M^{2+})_{1-x}(M^{3+})_x(OH^-)_2]^{x+}(A^-)_x \cdot mH_2O$, in which $0.1 \leq x \leq 0.33$, m is number of interlayer crystallization water molecules, and is in range of 0.5-6, $M^{2+}$ is $Mg^{2+}$, $M^{3+}$ is $Al^{3+}$, and $A^-$ is 2-hydroxy benzo[α]carbazole-3-carboxylate anion; and wherein the composite luminescent material has crystal structure of LDHs-like material, in which metal cations and hydroxide anions form multiple octahedrons via covalent bonds, the multiple octahedrons form sheet like structure via sharing edges, and 2-hydroxy benzo[a]carbazole-3-carboxylate anions are intercalated into LDHs layers to form anionic type supramolecular layered composite luminescent material with 2-hydroxy benzo[a]carbazole-3-carboxylate anion uniformly dispersion.

2. A preparation method of the benzocarbazole-intercalated layered double hydroxides (LDHs) composite luminescent material, wherein the method comprises:
   (1) preparing solution A with $Mg^{2+}/Al^{3+}$-molar ratio of 2:1-4:1, wherein $Mg^{2+}$ concentration is 0.01-1.6 mol/L;
   (2) preparing anhydrous ethylene glycol solution B of sodium 2-hydroxy benzo[a]carbazole-3-carboxylate, with concentration of 0.01-2.0M;
   (3) mixing solutions A and B to obtain solution C, and then pouring solution C into four-neck flask, wherein the usage amount of solutions A and B makes the molar ratio of sodium 2-hydroxy benzo[a]carbazole-3-carboxylate to $Al^{3+}$ in the solution C within 1:1-3:1;
   (4) preparing 0.01-3.0 mol/L NaOH solution, slowly adding the NaOH solution dropwise into the four-neck flask under nitrogen gas protection via constant-pressure funnel, wherein the usage amount of the solution C and NaOH solution makes the molar ratio of NaOH to sum of $Al^{3+}$ and $Mg^{2+}$ at 2;
   (5) regulating pH of the mixed solution obtained in (4) by NaOH to 8.0-10.0 after finishing the dropwise addition to obtain slurry D, placing the four-neck flask with the slurry D into 50-80° C. water bath, reacting under nitrogen gas protection for 12-24 hr, or transferring the slurry D from the four-neck flask into microwave rapid digestion tank, and microwave heating to react for 2-5 hr at 80-100° C.; and
   (6) subjecting the reaction product obtained in (5) to solid-liquid separation, sequentially washing the obtained solid product with $CO_2$-free deionized water and ethylene glycol for 3-6 times until the washing liquid is colorless, centrifuging after each washing, drying in vacuum the filter cake resulted from centrifugation after the final washing at 50-70° C. for 15-20 hr to obtain 2-hydroxy benzo[a]carbazole-3-carboxylate anion intercalated LDHs composite luminescent material.

* * * * *